United States Patent [19]
Bixby

[11] Patent Number: 5,806,668
[45] Date of Patent: Sep. 15, 1998

[54] CONTAINMENT, COLLECTION AND DISPOSAL DEVICE

[76] Inventor: Steven H. Bixby, 2640 Cardinal Dr., Missoula, Mont. 59803

[21] Appl. No.: 876,452

[22] Filed: Jun. 16, 1997

Related U.S. Application Data

[60] Provisional application No. 60/020,922 Jul. 1, 1996.
[51] Int. Cl.[6] .......................... A01K 29/00; A41D 19/00
[52] U.S. Cl. .......................... 206/216; 206/204; 206/278; 2/159; 15/227; 294/1.3
[58] Field of Search ..................................... 206/204, 216, 206/278, 361, 438, 459.5; 2/158–160, 164, 168; 15/227; 294/1.3, 25

[56] References Cited

U.S. PATENT DOCUMENTS

| | | |
|---|---|---|
| 1,832,153 | 11/1931 | Stöwener . |
| 2,651,071 | 9/1953 | Dyer et al. . |
| 2,893,546 | 7/1959 | Kendall et al. .......................... 206/278 |
| 3,329,985 | 7/1967 | Golwacki, Jr. .............................. 15/227 |
| 3,608,708 | 9/1971 | Storandt ..................................... 15/227 |
| 3,638,789 | 2/1972 | Tuszewski . |
| 4,154,542 | 5/1979 | Rasmason ................................... 15/227 |
| 4,321,161 | 3/1982 | Watanabe et al. . |
| 4,645,251 | 2/1987 | Jacobs . |
| 4,788,733 | 12/1988 | Lerner . |
| 4,902,283 | 2/1990 | Rojko et al. . |
| 4,959,341 | 9/1990 | Wallach . |
| 4,959,881 | 10/1990 | Murray . |
| 4,964,188 | 10/1990 | Olson . |
| 5,000,500 | 3/1991 | Almog . |
| 5,079,792 | 1/1992 | D'Haen . |
| 5,178,426 | 1/1993 | David et al. . |
| 5,186,322 | 2/1993 | Harreld et al. . |
| 5,301,806 | 4/1994 | Olson . |
| 5,369,257 | 11/1994 | Gibbon ........................................ 2/158 |
| 5,438,708 | 8/1995 | Jacovitz . |
| 5,473,789 | 12/1995 | Oster ......................................... 15/227 |

*Primary Examiner*—Paul T. Sewell
*Assistant Examiner*—Luan K. Bui
*Attorney, Agent, or Firm*—Fields and Johnson, P.C.

[57] ABSTRACT

A containment, collection and disposal device includes a liquid, impermeable bag which has an absorptive member attached to the outer surface of the distal end thereof for absorbing spills or other waste materials. A tab or handle is provided at the distal end of the bag at the inner surface thereof enabling the bag to reversed inside out so that, after a spill has been contained and collected, the material is isolated within the reversed bag. Seals are provided on the outer surface of the bag to enable the absorptive member to be sealed from the environment prior to use, and such seals may also then be used to seal the contaminant-laden absorptive member from the environment after the bag has been placed in the inside-out position.

13 Claims, 3 Drawing Sheets

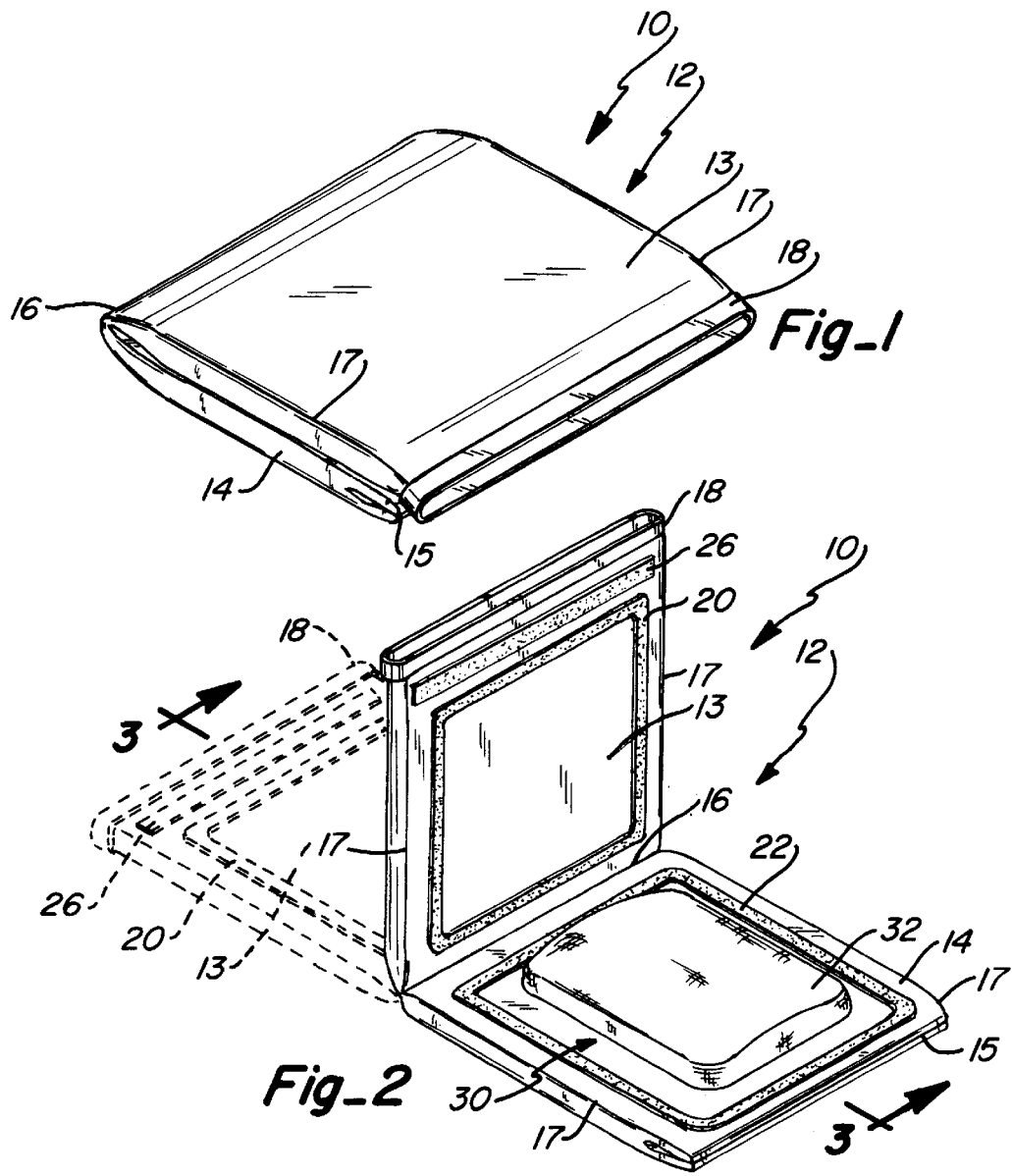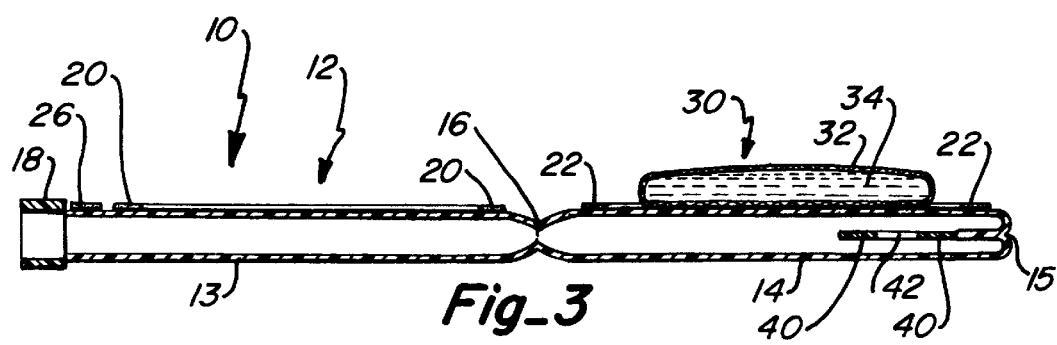

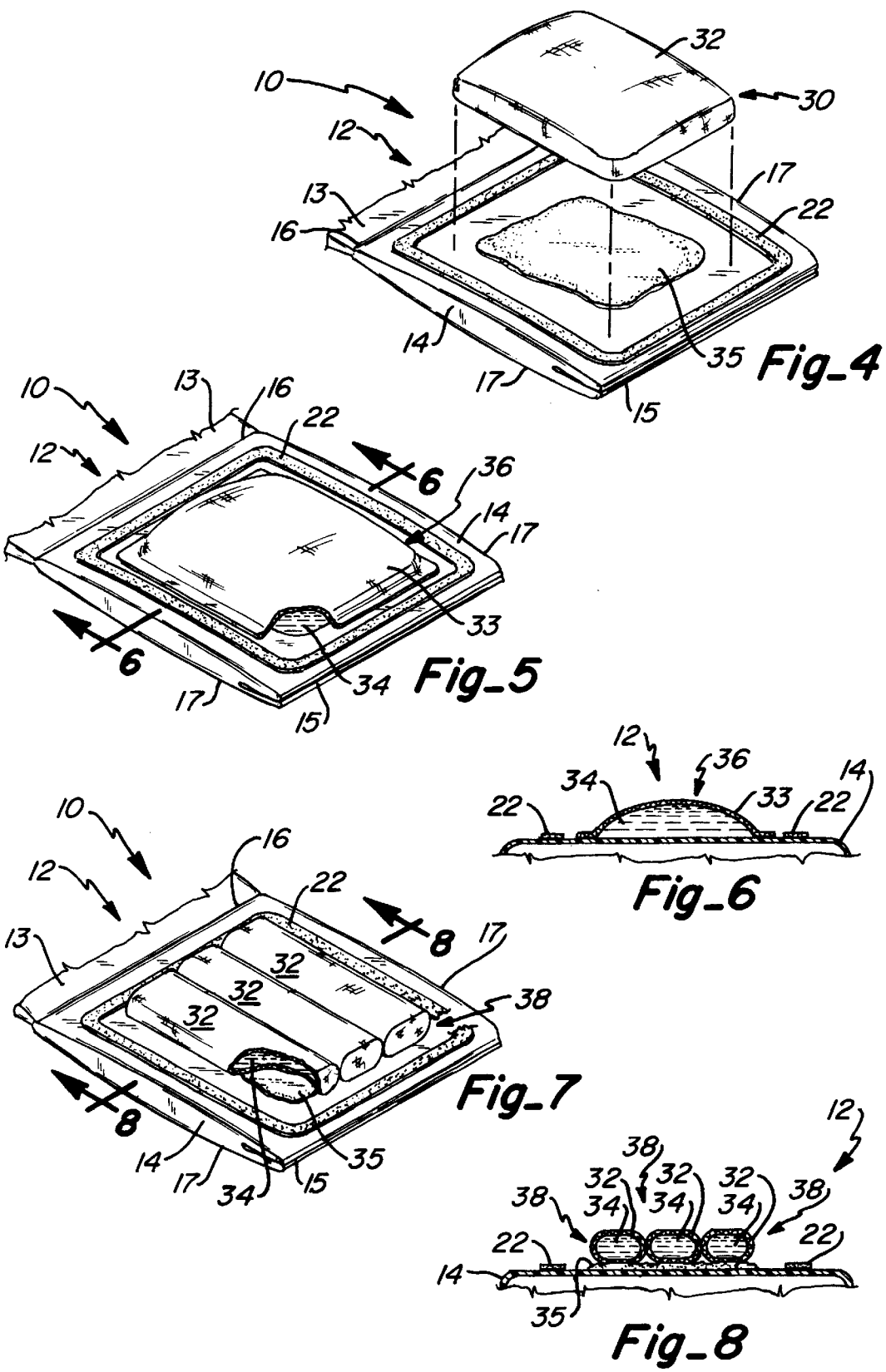

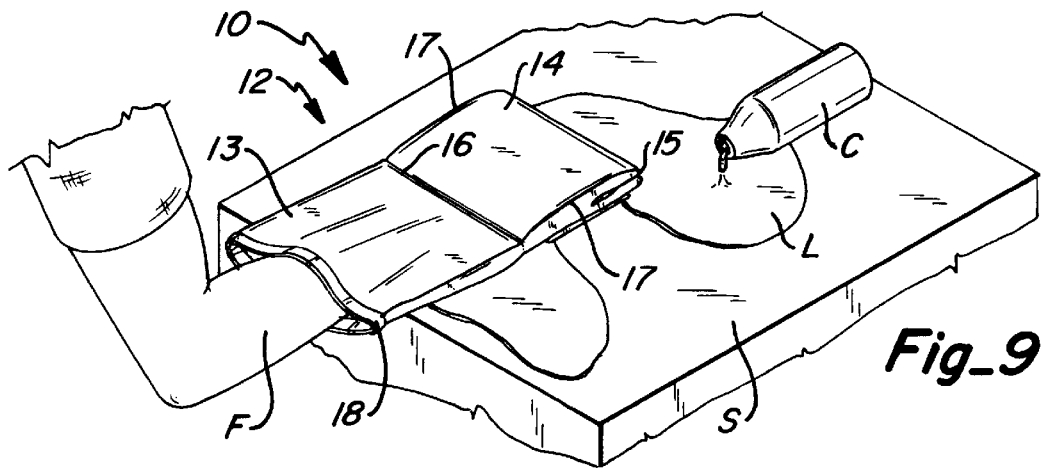
Fig_9
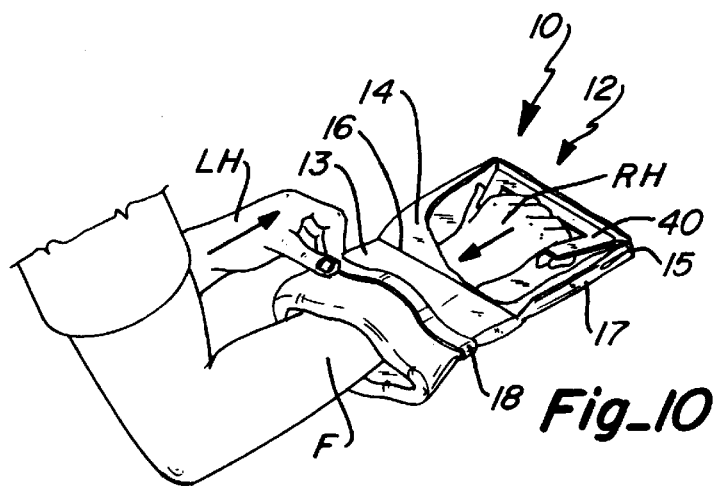
Fig_10
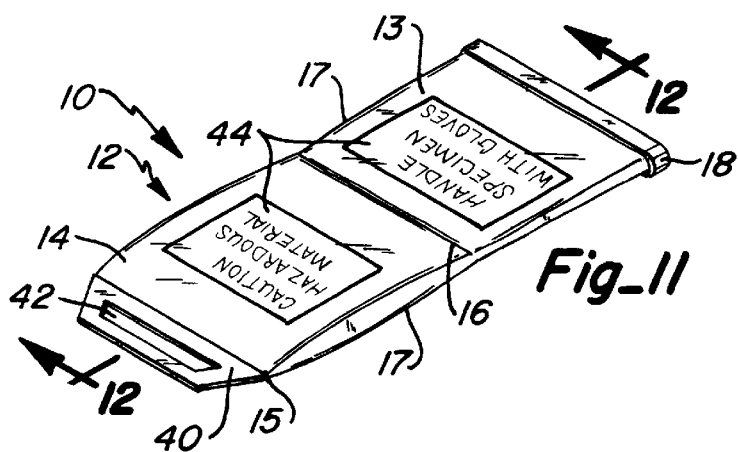
Fig_11
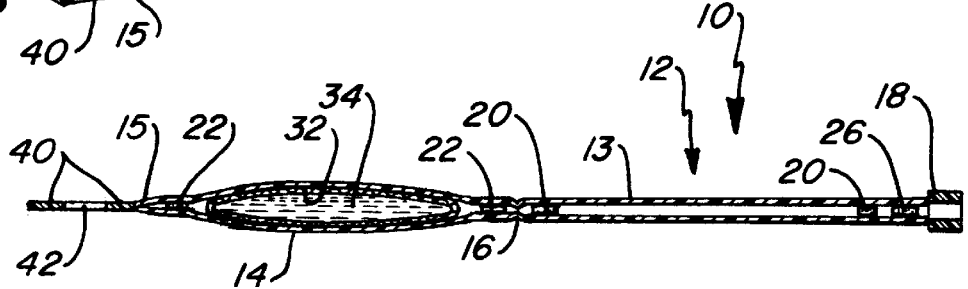
Fig_12

CONTAINMENT, COLLECTION AND DISPOSAL DEVICE

This application claims the benefit of the earlier filed provisional application, Ser. No. 60/020,922 filed on Jul. 1, 1996, entitled "Containment, Collection and Disposal Device".

TECHNICAL FIELD

This invention relates to a containment, collection and disposal method and device, and, more particularly, to a method and device for cleaning, containment, collection and disposal of both hazardous and non-hazardous materials.

BACKGROUND ART

In recent years, a heightened sense of awareness has come about resulting in efforts to protect humans from being unnecessarily exposed to toxic materials. Furthermore, with the progress of science, an increased sense of awareness has also come about resulting in efforts to protect humans from unnecessary exposure to not only commonly known toxic materials, but also other hazardous substances in the form of bioagents and chemical agents. Thus, a number of devices and methods have been introduced which enable humans to more effectively contain and collect toxic materials and hazardous substances and dispose of them in an environmentally prudent manner.

Some examples of prior art inventions which enable the clean-up of hazardous materials are U.S. Pat. Nos. 4,964,188 and 5,301,806 to Olson. These references disclose a clean-up bag including a plastic glove which is heat-sealed to one interior side of the bag. A padding of fibrous material is attached to the outside of the bag which absorbs any liquid surrounding or contained in the specimen to be picked up and disposed of. A drawstring closure is provided which has pleats on each side of the bag so that the bag may be easily turned inside out for disposal purposes.

U.S. Pat. No. 4,788,733 to Lerner discloses a glove constructed of a thin plastic material with the front surface of the glove substantially covered with a towel layer. The towel layer may be impregnated with a cleaning solution. Mounted on the glove in the area of the access opening to within the glove is a tie. The glove is capable of being turned inside out to enclose a soiled article and the tie is utilized to tightly close the access opening so that the glove can function as a disposal bag for the article.

U.S. Pat. No. 4,645,251 to Jacobs teaches a waste disposal system comprising a relatively thick heat-insulating flexible inner glove and an outer glove that is placed over the inner glove, the outer glove being made of a thin, flexible disposal material. In use, waste material is picked up by the user whose hand is contained within the inner glove and the outer glove is peeled or stripped off to an inside-out pouch forming configuration which traps the waste material therein.

U.S. Pat. No. 4,959,881 to Murray discloses a cleaning mitt including a cleaning pad which may be permeated with a cleaning solution. A cover is secured to the front face of the net covering the cleaning pad. In use, the cover is removed from its position covering the pad, thus, exposing the pad for use as a cleaning implement. Inner and outer tabs are provided to aid in the removal of the cover from the hand. Outer and inner cuffs may form pockets which aid in the convenient and sanitary disposal of the mitt.

U.S. Pat. No. 438,708 to Jacovitz discloses a device for collecting waste material comprising an ambidextrous glove having a sleeve portion with a pair of handles which are used to secure the sleeve portion to the bodily form of the user. The handles are also used to contain the collective material and for sealing the device. The glove is provided with an absorbent or non-absorbent contact means on the palm portion for contacting and removing the waste material to be collected.

The foregoing inventions are suitable for their intended purposes; however, in order to provide a cost-effective device which may be used to clean up hazardous material, it is necessary to have a disposable device which is structurally simple and thus can be manufactured at a minimum cost. The advantages of the invention disclosed herein in achieving these above-identified goals and others are explained in the specification and drawings which follow.

DISCLOSURE OF THE INVENTION

In accordance with the present invention, a containment, collection and disposal device is provided. In its simplest form, the device of this invention is constructed of a liquid impermeable bag which has an absorptive member attached to the outer surface of the distal end thereof for absorbing spills or other waste materials. A fold is formed laterally across the bag and serves the dual purpose of enabling the device to be in a compact shape during storage and to provide a means to seal the absorptive member from the environment prior to use, as will be further explained below.

The absorptive member may be impregnated with a desired chemical or cleaning agent depending upon the type of material to be contained and collected. For example, if the device of this invention is used in a laboratory to clean up spills of biohazardous material or hazardous chemicals, an appropriate cleaning, neutralizing or disinfectant agent may be impregnated within the absorptive member so that when the absorptive member is placed in contact with the spill, the absorptive member not only absorbs the spill, but also achieves some desired degree of disinfection or neutralization. The absorptive member may be formed of an independent pad which has an outer cover and a gelling or absorptive agent placed within the cover. Alternatively, the absorptive member may simply include a gelling or absorptive agent placed directly onto the bag with a single flap being secured to the bag forming a seal for retention of the gelling agent therein. In yet another embodiment, there may be a plurality of absorptive members attached to the bag in order to increase the surface area in which an absorptive element may contact a spill. When stored prior to use, the device is folded so that the folded portion completely covers the absorptive member in order to protect it from the environment which prevents the impregnated agent from drying up or from otherwise losing its effectiveness prior to use. A seal is provided on the folded portion of the bag to effectively seal the absorptive member.

A cuff is provided at the proximal open end of the bag which provides some degree of rigidity to the proximal end so that the user's hand may be easily inserted therethrough. Furthermore, an adhesive strip may be provided at the proximal end of the bag to further ensure that the bag remains in the folded position prior to use.

Attached to the distal end of the bag at the inner surface thereof or formed as part of the material within the bag is a tab or handle which enables the bag to be reversed inside out so that after a spill has been cleaned up, the material is isolated within the reversed bag. Once the bag has been reversed to an inside-out position, the same seal which provides a means to protect the absorptive member prior to use is also used as a means to seal the absorptive member laden with the spilled material inside the bag and away from the environment. Thus, this unique dual purpose seal greatly simplifies the structure of the device so that not only may the absorptive member be protected prior to use, but also, the absorptive member may then be effectively sealed from the environment.

Additional advantages of this invention will become apparent from the description which follows, taken in conjunction with the accompanying drawings.

BRIEF DESCRIPTION OF THE DRAWINGS

FIG. 1 is a perspective view of the containment, collection and disposal device of this invention when the device is in a folded storage position prior use;

FIG. 2 is a perspective view of the device of this invention illustrating the device as it is being opened from the folded position to a fully open position;

FIG. 3 is a horizontal section, taken along line 3—3 of FIG. 2, illustrating some structural details of the device;

FIG. 4 is a fragmentary, perspective view of a first embodiment of the device of this invention wherein the absorptive member is an independent member pad which is secured to the bag by means of an appropriate cement or glue;

FIG. 5 is a fragmentary perspective view of a second embodiment of the device of this invention illustrating an absorptive member which comprises a single flap or cover which is directly attached to the bag wherein an appropriate gelling or absorptive agent is placed therein prior to attaching the flap or cover to the bag;

FIG. 6 is a horizontal section, taken along line 6—6 of FIG. 5 showing some structural details of the second embodiment of this invention;

FIG. 7 is a fragmentary perspective view of a third embodiment of the device of this invention illustrating a plurality of absorptive members attached to the bag;

FIG. 8 is a horizontal section, taken along line 8—8 of FIG. 7, illustrating some structural details of the third embodiment of this invention;

FIG. 9 is a perspective view of the device in the fully open position during use on a spilled material;

FIG. 10 is a fragmentary perspective view illustrating the device as it is being turned to an inside-out position after collection of a spilled material;

FIG. 11 is a perspective view of the device illustrating it as being placed fully inside out; and FIG. 12 is a horizontal section, taken along line 12—12 of FIG. 11 illustrating some structural details of the device when placed in the inside-out position.

BEST MODE FOR CARRYING OUT THE INVENTION

As seen in FIG. 1, the containment, collection and disposal device 10 of this invention includes a bag 12 comprising a proximal sleeve portion 13 and a distal hand receiving portion 14. As shown, prior to use, the device is folded along fold 16 so that the proximal sleeve portion 13 is placed adjacent to the distal hand receiving portion 14. A cuff 18 may be formed at the open end of the bag at the proximal sleeve portion 13. The cuff may be manufactured from a semi-rigid plastic or polymer which provides some degree of rigidity to the open end of the bag. The bag itself is made of a liquid impermeable material such as polypropylene or some other suitable plastic or polymer which is liquid impermeable and resistant to the corrosive effects of a particular type of spilled material.

As seen in FIG. 2, when it is desired to place the device in operation, the bag 12 is opened so as to separate the proximal sleeve portion 13 from the distal end portion 14. An adhesive strip 26 may be provided at the proximal sleeve portion 13 to provide a means to keep the device in a folded position prior to use. An absorptive member 30 is provided and which is attached to the outer surface of the distal hand receiving portion 14. The exterior edges of the absorptive member 30 are surrounded by a distal seal 22 which corresponds to a proximal seal 20 formed on the proximal sleeve portion 13. When the device is in the folded position, the contact of proximal seal 20 with the distal seal 22 effectively seals the absorptive member 30 from the surrounding environment. This seal is particularly important when the absorptive member is impregnated with a cleaning solution or other chemical which is sensitive to or which can be degraded by contact with the atmosphere. Although a proximal seal 20 and distal seal 22 have been illustrated, it will be understood by those skilled in the art that a single seal may be provided at either the proximal sleeve portion 13 or distal hand portion 14 and which can effectively seal the absorptive member 30 from the environment when the bag 12 is in the folded position. Furthermore, the seals can be extended to the longitudinal edges 17 of the bag 12, which is an additional advantage as explained below, because the seals can also serve to seal the bag 12 after use.

The absorptive member shown in FIGS. 2 and 3 includes an absorptive member cover 32 which may be constructed of a suitable material such as cloth or paper. Disposed within the absorptive member cover 32 is a gelling or coagulating agent 34. The use of a gelling or coagulating agent 34 results in the absorption or attraction of a spilled material which effectively holds the material once it has been absorbed so that it does not again spill or otherwise leak from the absorptive member back onto the surface on which it was spilled. Materials such as neutralizing agents, buffering materials, disinfecting agents, anti-microbial solutions, and cleaning agents and the like can be impregnated or be contained within the absorptive member cover 32 in order to provide a means in which to effectively disinfect or neutralize a toxic or hazardous spill.

FIGS. 2 and 8 illustrate a first embodiment of the device of this invention wherein the absorptive member 30 is in the form of an independent, self-contained pad or pillow which contains the gelling/coagulating agent 34. Accordingly, this type of absorptive member 30 is attached to the distal hand receiving portion 14 simply by use of an appropriate adhesive or glue 35.

FIGS. 5 and 6 illustrate a second embodiment of the device of this invention wherein an absorptive member 36 comprises a single flap or cover 33 which is directly attached to the distal hand receiving portion 14. Prior to securing the flap 33 to the distal hand receiving portion 14, an appropriate gelling agent 34 is placed on the distal hand receiving portion 14 and is thereby trapped within the flap 33 upon sealing it to the distal hand portion 14.

FIGS. 7 and 8 show yet another embodiment of the device of this invention wherein a plurality of independent absorptive members 38, similar to the first embodiment, are each secured to the distal hand portion 14. As with the first embodiment, the absorptive members 38 of the third embodiment include absorptive member covers 32 and an appropriate gelling/coagulating agent 34 disposed therein.

An appropriate adhesive or glue 35 may be used to secure each of the absorptive members 38 to the distal hand portion 14. By use of a plurality of absorptive members 38, the effective surface area which contacts a spill is increased thereby enhancing the ability of the device to absorb and pick up spilled material.

Although a particular number of absorptive members 38 are illustrated in FIG. 7, it will be understood that any appropriate number of absorptive members may be used in order to maximize the effective surface area in which the absorptive members may absorb a spill. For example, it is within the spirit and scope of this invention that additional absorptive members are provided which also have a cylindrical shape as the absorptive members in FIG. 7; however, such additional absorptive members may resemble the shape of a cigarette or thin tube in which the absorptive members are placed in an appropriate arrangement on the distal hand receiving portion 14.

As shown in FIGS. 11 and 12, the tab or handle 40 is attached to the inner surface of the distal end 15 of the distal hand portion 14. The handle 40 may be made of a material similar to the cuff 18 which is semi-rigid, or the handle 40 may be simply made of the bag material wherein an opening 42 is formed and the distal end 15 is made to form the solid portion of the handle 40.

The use of this device can best be seen in FIGS. 9–12. Once the bag 12 has been placed in the open position, a user's hand may be inserted so that the proximal sleeve portion 13 covers a portion of the forearm F of the user. The user then may approach the spilled liquid L which may have come from a container C. The user then dabs or otherwise makes contact with the liquid L which is found on surface S. Once the spill has been effectively cleaned and absorbed, the user may grasp the tab or handle 40 by placing one or more fingers through opening 42. As shown in FIG. 10, the right hand RH is inserted within the device and secures the handle 40. The left hand LH may grasp the proximal sleeve portion 13 near the cuff 18 and the bag 12 is then inverted to the inside-out position as shown in FIG. 11. By inverting the bag 12 in such a manner, the absorptive member 30 which contains the spilled liquid may be effectively isolated from the surrounding environment and prevent any further transmission of the liquid. The bag 12 may then be disposed of according to prudent environmental practices.

As shown in FIG. 11, the appropriate labeling or indicia 44 may be placed on the interior surface of the bag 12 to warn of the nature of the contaminant contained therein. Accordingly, when the bag is placed in the inside-out position, the label will be exposed for viewing.

As shown in FIG. 12, the absorptive member containing the spilled contaminant is effectively sealed from the outside environment by seals 20 and 22 which make contact with an opposing side of bag 12. That is, when the bag 12 is placed in the inside-out position, seals 20 and 22 may be pressed against an opposing side of the bag 12 to form an effective seal. If it is desired to completely seal the absorptive member 30 from the environment, seals 20 and 22 can be extended to reach the peripheral edges 17 of the bag 12. Furthermore, adhesive strip 26 also serves as an additional seal to prevent contained liquid from being transmitted back to the environment.

Because the device of this invention is a single unit, it is ready for use when unpackaged and requires no assembly nor additional equipment. The compact design of the device when stored enables it to be easily placed in small places, such as may be found in lab benches or other storage areas.

Since the device is in the shape of a bag, the device is ambidextrous in that the left or right hand may be used without having to provide a complex and shape. With the incorporation of seals which may surround the absorptive member, the absorptive member may be impregnated with any number of different types of chemicals or agents to enable the device to be used in a virtually limitless number of applications. Furthermore, these unique seals also serve an additional purpose in sealing the contaminant-laden absorptive member from the environment after use.

This invention has been described in detail with reference to particular embodiments thereof, but it will be understood that various other modifications can effected within the spirit and scope of this invention.

What is claimed is:

1. A contaminant containment, collection and disposal device for removing and disposing of hazardous or non-hazardous materials from the surrounding environment, said device comprising:

a bag including an inner surface, an outer surface, a proximal end and a distal end;

an absorptive member attached to said outer surface of said bag adjacent said distal end thereof;

a handle attached to said inner surface of said bag at said distal end thereof; and a first seal formed on said bag and surrounding said absorptive member, said proximal end of said bag being foldable over said absorptive member so to isolate said absorptive member from the environment prior to and after use by sealing engagement of said first seal against said bag.

2. A device, as claimed in claim 1, further including:

a cuff attached to said proximal end of said bag to provide a desired degree of rigidity thereto.

3. A device, as claimed in claim 1, further including:

an adhesive strip attached to said outer surface of said bag for securing said proximal end to said distal end prior to use and to further isolate said absorptive member from the environment after use of said device.

4. A device, as claimed in claim 1, wherein said absorptive member includes:

a gelling agent positioned on said outer surface adjacent said distal end; and a cover positionable over said gelling agent for retaining said gelling agent therein.

5. A device, as claimed in claim 1, wherein said absorptive member includes:

a self-contained absorptive pad attachable adjacent to said distal end of said bag, said pad having a cover and a gelling agent placed therein.

6. A device, as claimed in claim 1, wherein said absorptive member includes:

a plurality of self contained absorptive members each having a respective cover and a respective gelling agent placed therein, each of said self contained absorptive members being attachable to said outer surface and adjacent said distal end of said bag.

7. A device, as claimed in claim 1, further including:

printed indicia on said inner surface of said bag for providing warning as to the contents therein.

8. A device, as claimed in claim 1, further including:

a second seal formed on said bag at an end opposite the placement of said first seal, said first and second seals being alignable for engagement with one another in order to seal said absorptive member with said proximal end of said bag that is folded over said distal end prior to use, and further to isolate said absorptive member from the environment when said bag is turned inside out after use.

9. A method of cleaning up a spill of hazardous or non-hazardous material, said method comprising the steps of:

providing a bag having an inner surface, an outer surface, a proximal end and a distal end;

providing a seal on the outer surface of the bag near the proximal end thereof;

providing an absorptive member on the outer surface of the bag adjacent the distal end thereof wherein said seal is engageable with the distal end of the bag by folding the proximal end thereover in order to seal the absorptive member from the environment prior to use;

exposing the absorptive member by breaking the seal;

inserting a hand into the bag;

applying the absorptive member over the spilled material;

absorbing the spilled material by means of the absorptive member;

grasping a handle positioned within the bag at the distal end thereof;

placing the bag into an inside-out position by pulling the proximal end of the bag back over the distal end;

isolating the absorptive member from the environment by the seal which engages a facing portion of the outer surface when the bag is placed in the inside-out position; and disposing of the bag according to prudent environmental practices.

10. A method, as claimed in claim 9, further including the step of:

warning a user as to the contents of the spilled material contained within the bag by printed indicia on the bag.

11. A method, as claimed in claim 9, further including the step of:

further isolating the absorptive from the environment by providing an adhesive strip attached to said outer surface of said bag and which engages a facing portion of the outer surface when the bag is placed in the inside-out position.

12. A contaminant containment, collection and disposal device comprising:

a bag including an inner surface, an outer surface, a proximal end and a distal end;

means for absorbing contaminants attached to said outer surface of said bag;

means for sealing said absorbing means and isolating it from the environment prior to and after use, said sealing means isolating said absorbing means by engaging an adjacent portion of said outer surface prior to use and isolating said absorbing means by engaging an opposite portion of said outer surface when said bag is turned inside-out after use.

13. A device, as claimed in claim 12, further including:

means for grasping attached to said inner surface of said bag near said distal end thereof enabling said bag to be turned inside-out after use.

* * * * *

UNITED STATES PATENT AND TRADEMARK OFFICE
CERTIFICATE OF CORRECTION

PATENT NO. : 5,806,668
DATED : 9/15/98
INVENTOR(S) : Steven H. Bixby

It is certified that error appears in the above-indentified patent and that said Letters Patent is hereby corrected as shown below:

Column 3, line 16, after "prior" insert --to--;
Column 3, line 24, after "member", second occurrence, insert --or--;
Column 6, line 3, delete "and" and insert --hand--.

Signed and Sealed this

Twenty-sixth Day of January, 1999

Attest:

Attesting Officer

*Acting Commissioner of Patents and Trademarks*